United States Patent
Nguyen et al.

(10) Patent No.: US 12,296,072 B2
(45) Date of Patent: May 13, 2025

(54) DISINFECTANT FOGGING COMPOSITION

(71) Applicant: Illinois Tool Works Inc., Glenview, IL (US)

(72) Inventors: Chi Quang Nguyen, Glenview, IL (US); John Isidoro Escoto, Jr., Glenview, IL (US)

(73) Assignee: Illinois Tool Works Inc., Glenview, IL (US)

(*) Notice: Subject to any disclaimer, the term of this patent is extended or adjusted under 35 U.S.C. 154(b) by 613 days.

(21) Appl. No.: 17/545,115

(22) Filed: Dec. 8, 2021

(65) Prior Publication Data

US 2022/0176001 A1 Jun. 9, 2022

Related U.S. Application Data

(60) Provisional application No. 63/122,544, filed on Dec. 8, 2020.

(51) Int. Cl.

| | | |
|---|---|---|
| *C11D 1/38* | (2006.01) | |
| *A61L 9/00* | (2006.01) | |
| *A61L 9/01* | (2006.01) | |
| *A61L 9/014* | (2006.01) | |
| *A61L 9/015* | (2006.01) | |
| *A61L 9/14* | (2006.01) | |
| *B08B 3/00* | (2006.01) | |
| *B08B 3/04* | (2006.01) | |
| *C11D 1/62* | (2006.01) | |
| *C11D 1/66* | (2006.01) | |
| *C11D 1/72* | (2006.01) | |
| *C11D 1/722* | (2006.01) | |
| *C11D 1/835* | (2006.01) | |
| *C11D 3/26* | (2006.01) | |
| *C11D 3/48* | (2006.01) | |

(52) U.S. Cl.
CPC ............... *A61L 9/015* (2013.01); *A61L 9/014* (2013.01); *C11D 1/62* (2013.01); *C11D 1/835* (2013.01); *C11D 3/48* (2013.01)

(58) Field of Classification Search
CPC .... C11D 1/38; C11D 1/62; C11D 1/66; C11D 1/72; C11D 1/722; C11D 1/835; C11D 3/162; C11D 3/2006; C11D 3/26; C11D 3/48; B08B 3/00; B08B 3/003; B08B 3/04; A61L 9/00; A61L 9/01; A61L 9/014; A61L 9/14; A61L 9/145
See application file for complete search history.

(56) References Cited

U.S. PATENT DOCUMENTS

| | | | | |
|---|---|---|---|---|
| 2007/0049511 | A1* | 3/2007 | Lawshe | ............... C11D 3/2079 510/424 |
| 2019/0040338 | A1* | 2/2019 | Paranjpe | ............... C11D 1/94 |

* cited by examiner

*Primary Examiner* — Brian P Mruk
(74) *Attorney, Agent, or Firm* — MaxGoLaw PLLC

(57) ABSTRACT

A composition is provided for a disinfectant fogger and cleaner for interior surfaces of confined spaces. The composition is water based and has an aqueous disinfectant containing quaternary ammonium compounds as active disinfecting ingredients, non-ionic surfactants, and a malodor absorbing agent. The composition provides a disinfectant for hard-nonporous and soft surfaces and allows for immediate occupancy and contact with a cleaned interior surface. The composition may be packaged as a ready-to-use disinfectant spray in an aerosol container with an on/off lockable discharge actuator as fine mist droplets that are dispersed onto the target surfaces for treatment.

14 Claims, No Drawings

DISINFECTANT FOGGING COMPOSITION

RELATED APPLICATIONS

This application claims priority benefit of U.S. Provisional Application Ser. No. 63/122,544 filed Dec. 8, 2020; the contents of which are hereby incorporated by reference.

FIELD OF THE INVENTION

The present invention in general relates to a disinfectant composition, and in particular, to a disinfectant fogger for interior surfaces of a vehicle cabin and other confined spaces.

BACKGROUND OF THE INVENTION

Disinfectant fogging involves saturating an entire room or a confined area with a microbial substance that can purify and remove pathogens from the air, as well as from surfaces within the room. This type of large-scale disinfection process is typically carried out sparingly in high risk areas because of the risk of inhaling the disinfectant solution, and the related time it takes to safely clean a room or confined area using this method. Despite these drawbacks, disinfectant fogging is highly effective at combating pathogens, particularly those that are airborne or carried in respiratory droplets, such as the flu virus or COVID-19 coronavirus.

Chemical foggers work by dispensing a fine mist of disinfectant solution until the atmosphere is supersaturated. This applies an even coating of solution to all surfaces in the room, as well as disinfects the air. The length of the treatment depends on the size of the area being fogged, but typically takes 30-60 minutes to complete, with an additional 60 minutes or more for the mist to dissipate and the air in the room to return to breathable levels.

Despite the availability of chemical foggers for rooms there is a scarcity of disinfectant foggers designed for the interior surfaces of vehicle cabins and small confined spaces. Conventional compositions for deodorizing vehicle interiors include chlorine dioxide generating canisters, and volatile substances that also must be thoroughly vented to avoid inhalation exposure. With the increasing popularity of rideshare options, as well as the need for improved sanitary conditions in vehicles used for rideshares there is a need for improved cleaning and disinfectants that can be quickly introduced into the cabin of a vehicle for cleaning and disinfecting without the need to vent the passenger compartment absent occupants.

Thus, there exists a need for a disinfectant fogger composition for the interior surfaces of vehicle cabins and small confined spaces that is suitable for immediate occupancy.

SUMMARY OF THE INVENTION

A spray on liquid surface cleaning and disinfectant composition is provided. The composition includes quaternary ammonium compounds, surfactant, aqueous solvent, and an odor absorbing agent. Other components might include wetting agents, pH modifiers, an antifoam agent, and a biocide. The composition components operate synergistically to disinfect a confined space more efficiently than conventional compositions that is suitable for immediate occupancy.

A process of cleaning and disinfecting vehicle interior surfaces includes applying the liquid surface cleaning and disinfectant composition as described above to the interior surface. The composition is allowed to dwell on the interior surfaces to achieve disinfection. Subsequently, the interior surfaces are suitable for immediate occupancy.

DETAILED DESCRIPTION OF THE INVENTION

The present invention has utility as a disinfectant fogger composition for interior surfaces of a vehicle compartment and other confined spaces subject to occupancy. Exemplary confined spaces include a passenger vehicle, a ride share vehicle, a train car, an aircraft cabin, a taxi, a bus, a peddle cab, a hotel room, a sleeper car, a restaurant table or booth, and combinations thereof. An inventive composition is provided of aqueous disinfectant containing quaternary ammonium salt compounds as active disinfecting ingredients, a non-ionic surfactant, at least one $C_2$-$C_8$ alcohols solvent, and a malodor absorbing agent. Embodiments of the inventive composition provide a broad-spectrum disinfectant, sanitizer, cleaner and deodorizer for hard-nonporous and soft surfaces. Embodiments of the composition may be packaged as a ready-to-use disinfectant spray in an aerosol container with an on/off lockable discharge actuator. In some inventive embodiments, additives such as a pH modifier, an antifoam agent, and a fragrance are also provided. A propellant such as inert gas or compressed air may be utilized in a dispensing device that allows for a total release of embodiments of the inventive composition in the container as fine mist droplets that cover and wet the entire cabin surfaces for treatment. In other inventive embodiments, a pump spray atomizer provides a suitable spray. As a result, the inventive composition in some embodiments is spray applied to interior vehicle cabin surfaces and confined spaces, and after sufficient dwell time acts as a cleaner, disinfectant, sanitizer and deodorizer. In contrast to the prior art, an inventive composition is not toxic to occupants and therefore a target area can be spaced and immediately occupied or re-occupied.

Numerical ranges cited herein are intended to recite not only the end values of such ranges, but the individual values encompassed within the range and varying in single units of the last significant figure. By way of example, a range of from 0.1 to 1.0 in arbitrary units according to the present invention also encompasses 0.2, 0.3, 0.4, 0.5, 0.6, 0.7, 0.8, and 0.9; each independently as lower and upper bounding values for the range.

As used herein, "immediate occupancy" is defined as entering a confined space and/or contacting an interior surface having been exposed to an inventive composition within 5-10 minutes of the exposure.

An inventive cleaning composition is based on non-ionic surfactants. Non-ionic surfactants operative herein soluble in water, and $C_2$-$C_8$ alcohols used herein.

Non-ionic surfactants operative herein in some inventive embodiments have hydrophile/lipophile balance (HLB) values between 8 and 14. Classes of non-ionic surfactants operative herein include $C_9$-$C_{24}$ fatty acid esters, $C_{12}$-$C_{24}$ fatty alcohol ethers, $C_{10}$-$C_{24}$ amine oxides, nonylphenol ethoxylate, alkyl polyglucosides with $C_5$-$C_{16}$ alkyl chain, each alone or any of the aforementioned in combination. Other alcohol alkoxylates operative herein have the general formula:

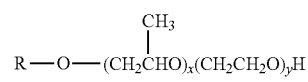

where R is $C_4$-$C_{22}$ linear or branched chain alkyl or mixtures thereof; x has a value of from 2 to 20; y has a value of from 0 to 15, or the general formula:

$$RO-(CH_2CH_2O)_n-H$$

where n is average moles of ethylene oxide (EO) and R is a $C_9$-$C_{18}$ alkyl.

Specific non-ionic surfactants operative herein illustratively include alcohol $C_{12}$-$C_{15}$ ethoxylated propoxylated, $C_{12}$-$C_{14}$, ethoxylated, $C_{9-11}$ ethoxylated alcohols having EO values from 2.5-9 or combinations thereof. In some inventive embodiments, EO 2.5 $C_{9-11}$ ethoxylated alcohol is used in combination with one or more EO 6-9 $C_{9-11}$ ethoxylated alcohols. The ratio of EO 2.5:EO 6-9 $C_{9-11}$ ethoxylated alcohols being between 0.1-1:1. In still other embodiments, the mixing 2.5 EO and 6-9 EO $C_{9-11}$ ethoxylated alcohols are used in combination with a non-ionic amine oxide. Typical loadings of all non-ionic surfactants present in an inventive composition range from 0.5 to 12 total weight percent.

Quaternary ammonium salts that may be used in embodiments of the inventive composition illustratively include dialkyl (each independently $C_{10}$-$C_{20}$) dimethyl ammonium chloride, alkyl ($C_{10}$-$C_{20}$) dimethyl benzyl ammonium chloride, and combinations thereof. Specific quaternary ammonium salts operative herein illustratively include octyl decyl dimethyl ammonium chloride, dioctyl dimethyl ammonium chloride, didecyl dimethyl ammonium chloride, and combinations thereof. Quaternary ammonium salts are typically being present from 0.05 to 3 total weight percent and preferably between 0.1 and 0.5 total weight percent.

The solvent system of an inventive composition includes water, specifically deionized water (DI) as the majority by weight solvent. Lesser amounts of secondary solvents include dipropylene glycol n-propyl ether, dipropylene glycol n-butyl ether, diethylene glycol ethyl ether, diethylene glycol n-butyl ether, and water miscible alcohols.

A malodor absorbing agent is provided that is not a chemical odor masking agent but rather odor neutralizer that traps and absorbs odors. A zinc ricinoleate-based odor neutralizer is suitable as a malodor absorbing agent. Zinc ricinoleate-based odor neutralizers provide selective fixation of odor-active agents. Zinc ricinoleate is a salt of ricinoleic acid, a major fatty acid found in castor oil. Zinc ricinoleate is used in many deodorants as an odor-adsorbing agent. Zinc ricinoleate-based odor neutralizers are complex zinc salts that are dispersed as a 20% zinc salt dispersion designed to deliver the benefits of odor control and remediation. As 50% concentration by weight of zinc ricinoleate dispersion in nonionic surfactant in $C_{12-14}$ ethoxylated alcohol. It is appreciated that zinc salts are provided in other concentrations and solvents according to the present invention, yet the aforementioned version minimally impacts quaternary ammonium salt functionality. Embodiments of the inventive zinc ricinoleate-based malodor absorbing agents have cold temperature stability and may be used as an additive in both hard- and soft-surface cleaning formulations. In specific inventive embodiments, the zinc ricinoleate-based odor neutralizers may also be readily diluted in water to a neutral pH or to slightly alkaline pH, or slightly acidic pH. Embodiments of the zinc ricinoleate-based odor neutralizers may also be emulsified to form microemulsions when diluted in water, and since the inventive zinc ricinoleate-based malodor absorbing agents are highly reactive, they are readily emulsifiable as zinc salt complex compounds.

Optional additives in an inventive composition illustratively include water miscible solvent, a biocide, a wetting agent, a pH modifier, a fragrance, defoaming agent, or a combination thereof.

A lesser amounts of water miscible secondary solvents includes $C_2$-$C_8$ alcohols. Specific alcohols operative herein include ethanol, propanol, isopropanol, butanol, sec-butanol, tert-butyl alcohol isobutanol, pentanol, isoamyl alcohol, 2-methyl-1-butanol, neopentyl alcohol, 2-pentanol, 3-methyl-2-butanol, 3-pentanol, tert-amyl alcohol, 2-Hexanol, 3-Hexanol, 2-Methyl-1-pentanol, 3-Methyl-1-pentanol, 4-Methyl-1-pentanol, 2-Methyl-2-pentanol, 3-Methyl-2-pentanol, 4-Methyl-2-pentanol, 2-Methyl-3-pentanol, 3-Methyl-3-pentanol, 2,2-dimethyl-1-butanol, 2,3-dimethyl-1-butanol, 3,3-dimethyl-1-butanol, and combinations thereof.

A biocide operative herein illustratively includes triclosan, para-chloro-meta-xylenol (PCMX), other conventional antibacterials, and combinations thereof. In specific inventive embodiments, an antimicrobial such as polyethyleneimine is included. Toxicity may be by two different mechanisms: the disruption of the cell membrane leading to necrotic cell death (immediate) and disruption of the mitochondrial membrane after internalization leading to apoptosis (delayed). The biocide is typically being present from 0.05 to 3 total weight percent and preferably between 0.1 and 0.5 total weight percent.

A wetting agent operative herein illustratively includes sulfo succinamates, disodium N-octadecylsulfo-succinamate; tetrasodium N-(1,2-dicarboxyethyl)-N-octadecylsulfo-succinamate; diamyl ester of sodium sulfosuccinic acid; dihexyl ester of sodium sulfosuccinic acid; and dioctyl esters of sodium sulfosuccinic acid; dihexyl ester of sodium sulfosuccinic acid; and dioctyl esters of sodium sulfosuccinic acid; castor oil and fatty amine ethoxylates; lecithin; fatty acids, salts thereof, ethanolamides thereof, and glycerides thereof; sodium polycarboxylate; sodium salt of naphthalene sulfonate condensate; calcium naphthalene sulfonates; sodium lignosulfonates; aliphatic alcohol ethoxylates; ethoxylated tridecyl alcohols; ethoxylated tristearyl phenols; sodium methyl oleyl taurate; tristyrylphenol ethoxylates; ethylene oxide-propylene oxide block copolymers; sodium dodecylbenzene sulfonate; N-oleyl N-methyl taurate; 1,4-dioctoxy-1,4-dioxo-butane-2-sulfonic acid; sodium lauryl sulphate; sodium dioctyl sulphosuccinate; aliphatic alcohol ethoxylates; nonylphenol ethoxylates; salts of maleic anhydride copolymers; n-octyl-2-pyrrolidone, polyvinylpyrrolidone; polyvinyl alcohols, modified or unmodified starches, methylcellulose; hydroxyethyl or hydroxypropyl methylcellulose; carboxymethyl methylcellulose; polyalkyleneimines, such as polyethyleneimine; and combinations thereof. In specific inventive embodiments, polyethyleneimine is included. The function of the wetting agent is to spread the bioactive ingredients on a variety of references such as plastics, metals, leathers, fabrics, and touchscreens. The wetting agent is typically being present from 0.05 to 3 total weight percent and preferably between 0.1 and 0.5 total weight percent.

pH modifiers operative herein illustratively include amino-2-hydroxyethane, 2-[bis(2-hydroxyethyl)amino] ethanol, 2-amino-2-methyl-1-propanol, soda ash, sodium hydroxide, and lime. In some embodiments, a pH modifier is present in an amount to achieve a composition pH of between 8.0 and 12.0.

A fragrance, if present is included in amounts of up to 4 total weight percent and in other embodiments from 0.1 to 0.6 total percent.

A defoaming agent is present in certain embodiments in an amount present to inhibit surfactant foaminess. Defoamer agents operative herein illustratively include silicone-based defoamers; mineral oil-based defoamers, and mixtures of foam destroying polymers and hydrophobic solids such as polyureas, as are known to the art. Specific exemplary silicone-based defoamers illustratively include silicone Antifoam emulsion, silica-filled polydimethyl siloxane and polyether-modified polysiloxanes.

An inventive composition is readily applied to a substrate by swabbing, misting pump spray, air pressurized spray, trigger spray, or by application from a spray aerosol can. Propellants are used to aerosolize the composition to provide strong pressure when spraying. As such, a propellant is optionally added in a typical range from 5 to 60 total weight percent. Suitable propellants illustratively include difluoroethane, trifluoroethane, alkanes such as butane, pentane, isobutane, propane; ethers such as dimethyl ether, diethyl ether, nitrogen; halogenated hydrocarbons; carbon dioxide and combinations thereof. The resultant formulation inclusive of a propellant is seated within a conventional metal aerosol canister and applied by spray application. In a specific inventive embodiment, the composition is a ready-to-use disinfectant spray in a plastic aerosol container with an on/off lockable discharge actuator. An inventive composition is readily stored in glass, metal, or plastic containers made of plastics such as polyethylenes, polypropylenes, nylons, PVC, or PET, or aerosol cans.

The formulation of an inventive composition is summarized below in Table 1.

TABLE 1

Inventive Cleaning Composition (exclusive of propellants).

| Component | Typical Amount Total Wt. Percent | Pref. Amount - Total Wt. Percent |
| --- | --- | --- |
| Non-ionic surfactants | 0.5-12 | 1-3 |
| Quaternary ammonium salt | 0.05-3 | 0.1-0.5 |
| Malodor absorbing agent | 0.05-4 | 0.1-0.6 |
| Water | Remainder | Remainder |
| Optional components | | |
| $C_2$-$C_8$ alcohol | 1-8 | 2-4 |
| Biocide | 0.05-3 | 0.1-0.5 |
| Wetting agent | 0.05-3 | 0.1-0.5 |
| pH modifier | to pH 8.0-12.0 | to pH 9.0-11.0 |
| Fragrance | 0-4 | 0.1-0.6 |
| Defoaming agent | 0-4 | 0.1-0.6 |

A specific exemplary formulation of an inventive composition is provided, unless noted otherwise, all percentages for the specific formulation are total weight percentages. Inventive composition 1.

The advantages of this invention are more particularly shown by the following examples in which the parts and percentages are by weight unless otherwise indicated.

Example 1

A composition is created that includes diproplylene glycol n-propyl ether (0.8%) $C_{12}$-$C_{14}$ ethoxylated alcohol (0.32%), $C_{12}$-$C_{15}$ ethoxylated propoxylated alcohol (0.03%), an antimicrobial of polyethyleneimine (0.2%), malodor absorbing agent of zinc ricinolate (0.15%), and a mixture of quaternary ammonium salts of alkyl ($C_{10}$-$C_{20}$) dimethyl benzyl, octyl decyl dimethyl ammonium chloride, dioctyl dimethyl ammonium chloride, didecyl dimethyl ammonium chloride present in equal parts and in a total amount of (0.09%) are dissolved in ethanol (3%) and the remainder being deionized water. 2-amino-2-methyl-1-propanol is added as a pH modifier (0.1%). The parenthetical amounts being amounts by total weight percent. The resulting formulation is applied to a trigger spray as a mist to a vehicle seat within an enclosure simulative of a vehicle interior and provided greater than 99.9% kill according to AOAC Germicidal Spray Products Test, AOAC Fungicidal Activity of Disinfectants Test, and Virucidal Efficacy Tests. The enclosure is suitable for occupancy immediately after misting.

Example 2

The process of Example 1 is repeated with the formulation of inventive composition with the inclusion of a silicone antifoam emulsion to 0.005% with a commensurate reduction in water. The composition functioned similar to that of Example 1.

Example 3

The composition of Example 2 is charged in a metal aerosol canister loaded with nitrogen as a propellant. The composition functioned similar to that of Example 1.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention but is not meant to be a limitation upon the practice thereof. The following claims, including all equivalents thereof are intended to define the scope of the invention.

The invention claimed is:

1. A disinfectant fogging composition comprising:
    a non-ionic surfactant;
    a dialkyl dimethyl ammonium chloride where each alkyl of the dialkyl is independently $C_{10}$-$C_{20}$;
    a malodor absorbing agent; and
    a majority by weight of water, the composition having a pH of 9 to 11; and
    $C_{9-11}$ ethoxylated alcohols having ethylene oxide values from 2.5-9, or combinations thereof; and
    wherein said non-ionic surfactant is a $C_{12}$-$C_{15}$ ethoxylated propoxylated alcohol, a $C_{12}$-$C_{14}$ ethoxylated alcohol, or a combination thereof.

2. The composition of claim 1 wherein said non-ionic surfactant is present from 1 to 3 total weight percent.

3. The composition of claim 1 wherein said malodor absorbing agent comprises a zinc ricinolate.

4. The composition of claim 1 further comprising a pH modifier.

5. The composition of claim 4 wherein said pH modifier is at least one of amino-2-hydroxyethane, 2-[bis(2-hydroxyethyl)amino]ethanol, 2-amino-2-methyl-1-propanol, soda ash, sodium hydroxide, lime, or a combination thereof.

6. The composition of claim 1 further comprising a wetting agent.

7. The composition of claim 1 further comprising a defoaming agent wherein said defoaming agent is at least one of antifoam emulsion, silica-filled polydimethyl siloxane and polyether-modified polysiloxanes.

8. The composition of claim 1 further comprising a biocide.

9. The composition of claim 1 further comprising a fragrance.

10. A disinfectant fogging composition comprising:
   a non-ionic surfactant;
   a dialkyl dimethyl ammonium chloride where each alkyl of the dialkyl is independently $C_{10}$-$C_{20}$;
   a malodor absorbing agent;
   a majority by weight of water, the composition having a pH of 9 to 11; and
   a $C_2$-$C_8$ alcohol; and
   wherein said non-ionic surfactant is a $C_{12}$-$C_{15}$ ethoxylated propoxylated alcohol, a $C_{12}$-$C_{14}$ ethoxylated alcohol, or a combination thereof.

11. A process of disinfecting an interior surface via fogging comprising:
   applying a disinfectant fogging composition of claim 1 to the interior surface; and
   allowing the composition to dwell and be retained on the interior surface.

12. The process of claim 11 further comprising a human contacting the interior surface within 5 minutes of the dwell.

13. The process of claim 11 wherein the applying of the composition is by spraying from a pump spray, an air pressurized spray, a trigger spray, or a spray aerosol can.

14. The process of claim 11 wherein the interior surface is a passenger vehicle, a ride share vehicle, a train car, an aircraft cabin, a taxi, a bus, a peddle cab, a hotel room, a sleeper car, a restaurant table, or a restaurant booth.

* * * * *